United States Patent [19]
Geier et al.

[11] Patent Number: 5,474,225
[45] Date of Patent: Dec. 12, 1995

[54] AUTOMATED METHOD FOR BUTT WELD INSPECTION AND DEFECT DIAGNOSIS

[75] Inventors: Daniel P. Geier, Lynchburg; Kenneth R. Camplin, Forest, both of Va.

[73] Assignee: The Babcock & Wilcox Company, New Orleans, La.

[21] Appl. No.: 276,286

[22] Filed: Jul. 18, 1994

[51] Int. Cl.⁶ .......................... B23K 11/36; B23K 31/00
[52] U.S. Cl. .............................. 228/104; 228/5.7; 228/9
[58] Field of Search ................................ 228/102, 104, 228/171, 7, 9, 5.7

[56] References Cited

U.S. PATENT DOCUMENTS

| | | | |
|---|---|---|---|
| 3,575,044 | 4/1971 | Gibbs et al. | 228/104 |
| 3,850,028 | 11/1974 | Thompson et al. | 73/71.5 |
| 4,058,002 | 11/1977 | Moran | 73/620 |
| 4,289,030 | 9/1981 | Alers et al. | 73/588 |
| 4,295,214 | 10/1981 | Thompson | 367/140 |
| 5,085,082 | 2/1992 | Cantor et al. | 228/104 |
| 5,154,081 | 10/1992 | Thompson et al. | 73/597 |

OTHER PUBLICATIONS

Technical Article by D. T. MacLaughlin, G. A. Alers and J. J. Jackson, "Detection and Measurement of Defects in Butt Welds", *Review of Progress in Quantitative Nondestructive Evaluation*, 1989, pp. 1039–1046.

Proposal #93155A06295.017, Rev. A, dated Sep. 13, 1993 and made to Armco Steel Company L.P. by the Taylor—Winfield Corp.; Re: Automated Flash Butt Welder Inspection System for #4 Pickle Line Welder.

Proposal #CB–011–B–00, dated Sep. 24, 1993 and made to Armco Steel Company L.P. by The Babcock & Wilcox Company; Re: Welder Diagnostic System.

Brochure entitled "Automated Butt–Weld Inspection System,", published Aug. 1993 by the Taylor—Winfield Corp., Warren Ohio.

Brochure entitled "EMAT Inspection Systems for Non–Destructive Testing", published Sept. 1993 by the Babcock & Wilcox Company, CIM Systems, Lynchburg, Va.

Brochure entitled: "Butt Weld Inspection and Weld Machine Diagnostic System", published Jul. 1994 by The Babcock & Wilcox Company, Innerspec Technologies, Lynchburg, Va.

Specification entitled "Armco Spec RES1174 (Inquiry #M–1174–00)", dated Nov. 7, 1993, issued by Armco Steel Company L.P. for No. 4 Pickle Line Automated Flash Butt Welder Inspection System.

*Primary Examiner*—Samuel M. Heinrich
*Attorney, Agent, or Firm*—Robert P. Bennett, Jr.; Robert J. Edwards

[57] ABSTRACT

An automated method for non-destructive inspection and evaluation of a weld through the use of ultrasonic waves produced by an electromagnetic acoustic transducer (EMAT). The method includes automatic positioning of a transport apparatus containing EMAT transmitter and receiver coils in proximity of a just-completed weld; scanning the weld; receiving an electrical signal produced in the EMAT receiver coil by a reflected ultrasonic SH shear wave; recording and monitoring the electrical signal; analyzing tie electrical signal relative to predetermined control limits; signaling the presence of a defect in the weld; and communicating electronically with a welding apparatus to reperform and/or alter the way in which subsequent welds are made so as to avoid repetition of the defect. The method also includes automatic receiving, recording, and monitoring of welding apparatus and welding process data, as well as automatic adjustment of corresponding welding apparatus and welding process parameters.

13 Claims, 2 Drawing Sheets

AUTOMATED METHOD FOR BUTT WELD INSPECTION AND DEFECT DIAGNOSIS

BACKGROUND OF THE INVENTION

1. Field of the Invention

The present invention relates in general to a method for weld inspection and defect analysis, and more specifically to an automated method for non-destructive inspection and evaluation of a butt weld through the use of ultrasonic waves.

2. Description of the Related Art

A variety of industries use sheet metal which is produced typically at a factory from ingots processed by a rolling mill. Ingots are heated and rolled by the mill into a long flat sheet which is then wound into a coil at the end of the mill. Thereafter, the coil is removed from the mill and shipped to other sections of the factory where further treatment processes are performed. To make these other processes have fewer interruptions, the coil is unrolled and joined at one of its ends to the end of another coil by an electric resistance weld which generally is in the form of a butt weld. Any number of coils may be welded together in such fashion, depending upon the desired length of process run. Weld defects, however, can cause a weld to break during a process run, resulting in costly equipment damage, production delays and wasted material.

In order to identify and remedy weld defects before they can cause breaks and consequential production problems, non-destructive testing of the welds can be performed. An inspection device is known that uses ultrasonic waves to non-destructively test the welds shortly after they have been made. The device employs Electromagnetic Acoustic Transducers (EMAT) which are arranged to transmit and receive what are known to be SH shear waves. The SH shear waves are launched by a transmitter meander coil EMAT, and the waves travel through the sheet metal to the weld where they are reflected back through the sheet metal and are received by a separate receiver meander coil EMAT located near the transmitter. During this non-destructive test, the reflected wave produces an electrical signal in the receiver coil, which is monitored while both the transmitter coil and the receiver coil are scanned close to the surface of the sheet metal, parallel to the weld line, and over the full width of the sheet metal. During the scanning, the amplitude of the signal produced in the receiver coil is measured and used to indicate the quality of the weld.

The known device is retrofitted into a flash butt welding machine on a production line, and a motorized transport apparatus into which the transmitter and receiver coils are mounted is used to carry out each weld scan. Unlike the method of the present invention, operation of the known device requires full-time control by a human operator, who, through the manipulation of push buttons, moves and positions the transport apparatus with the transmitter and receiver coils onto and across the sheet metal surface subsequent to the making of each weld by the welding machine. Results of the test, i.e., the measured amplitude of the receiver coil signal, are recorded on a device such as a strip chart recorder and are monitored and interpreted by the human operator.

References of interest are U.S. Pat. No. 4,295,214 to Thompson, which discloses an Ultrasonic Shear Wave Transducer, and D. T. MacLauchlan, G. A. Alers and J. J. Jackson, "Detection and Measurement of Defects in Butt Welds", *Review Of Progress In Quantitative Nondestructive Evaluation*, 1989, p. 1039.

SUMMARY OF THE INVENTION

It is an object of this invention to provide a new and improved method for non-destructively inspecting and evaluating butt welds through the use of ultrasonic SH shear waves. The present invention has among its principal novel features automatic positioning of a transport apparatus containing EMAT transmitter and receiver coils in proximity of a just-completed weld; scanning the weld; receiving the electrical signal produced in the receiver coil by the reflected SH shear wave; recording and monitoring the electrical signal; analyzing the electrical signal relative to certain predetermined weld quality control limits which have been preprogrammed into the inspection system; signaling the presence of a defect in the weld; and communicating electronically with the welding apparatus to reperform the just-completed weld and/or to alter the way in which subsequent welds are made so as to avoid repetition of the observed defect. Also included among the novel features of the present invention is automatic receiving, recording and monitoring of selected information pertaining to the welding apparatus and to the making of each weld by the welding apparatus. Such information is received, recorded and monitored concurrent with the making of each weld.

Certain advantages over the known manual method of inspecting welds and diagnosing weld defects by ultrasonic device are afforded by the present invention. The advantages include significantly improved performance, reliability and efficiency of the butt welding inspection and evaluation process and elimination of the need for an inspection device operator.

The present invention is performed in part with the aid of a computer control unit which is instrumental in providing automated control of the transport apparatus which will be situated downstream of the welding apparatus. The computer control unit has an electrical interface with the controller of the welding apparatus, as well as, with the transport apparatus and a data acquisition device. The interface to the controller of the welding apparatus is used to coordinate the sequence by which the inspection process is actuated. At the conclusion of each weld, signals are received by the computer control unit from the welding apparatus. These signals are used generally to coordinate the non-destructive weld test with a terminal step in the welding process, known as the flash removal step, where excess weld metal is trimmed from the just-completed weld. More specifically, the signals received from the computer control unit during the flash removal step are used to initiate and implement the positioning of the transport apparatus in proximity of the weld and thereafter commence scanning of the weld by the EMAT transmitter and receiver coils. An advantage gained by coordinating the weld test and the flash removal step is minimization of the amount of time added by the test to the overall cycle time, i.e., the time that elapses between commencement of the welding operation and completion of the non-destructive test. The use of the computer control unit and its integration with the welder controller eliminates the need for a human to observe the welding operation and to determine when to begin positioning the transport apparatus near the weld.

The transport apparatus has affixed to it an edge detection sensor which is used to help position the EMAT coils onto the sheet metal surface at one of the sheet's edges before the weld scanning step commences. The edge detection sensor, which is in electrical communication with the computer control unit, produces an electrical signal when the leading edge of the sheet metal is sensed. The signal is transmitted to the computer control unit which positions the EMAT coils and makes them ready for the scan.

During the weld scanning step, the transport apparatus is moved mechanically across the width of the sheet metal. As the transport apparatus and the EMAT coils contained therein cross the sheet metal near the weld, the ultrasonic SH shear waves produced by the EMAT transmitter coil travel through the sheet metal where they are reflected back through the sheet metal and are received by the EMAT receiver coil. The reflected wave produces an electrical signal in the receiver coil and that signal is transmitted to the computer control unit by way of the electrical interface between the transport apparatus and the computer control unit. From the computer control unit, the signal, which is in essence raw weld inspection data, is then relayed to a data acquisition unit via the electrical interface between the computer control unit and the data acquisition unit.

The edge detection sensor used to help position the EMAT coils before commencement of the weld scan is also employed to ascertain the end of the scanning step. Movement of the transport apparatus across the width of the sheet metal eventually causes the edge detection sensor to sense the trailing edge of the sheet metal. Upon detecting the trailing edge, the edge detection sensor produces an electrical signal which is transmitted to the computer control unit which in turn activates the removal of the EMAT coils from the surface of the sheet metal and the positioning of the transport apparatus at a safe location off the welding process line during the period where no weld inspection is required.

A data acquisition unit is employed with the present invention. The data acquisition unit is utilized for automatically: (1) receiving, recording, monitoring and displaying preselected welding apparatus and welding process data as such data are generated upon the making of each weld; (2) receiving, recording, monitoring, displaying and analyzing the weld inspection data produced during the weld scanning step; (3) signaling the presence and location of a weld defect contemporaneously with the weld scanning step; and (4) communicating electronically with the welding apparatus to reperform a just-completed weld and/or to alter the way in which subsequent welds are made.

The data acquisition unit is generally comprised of a 486-based IBM/PC compatible computer, a computer keyboard, a video display monitor, computer software capable of processing the data transmitted to the data acquisition unit, and electronic interconnections to the computer control unit and to the welding apparatus.

Welding apparatus and welding process data are transmitted to the data acquisition unit by way of an electronic interconnection between the welding apparatus and the data acquisition unit. Transmitted data may include: welding process currents and voltages; weld apparatus platen movements; hydraulic pressures and temperatures; load cam to load plate measurement; welder events, such as die position, status and cycle time; upset cylinder differential pressure; upset force; servo amplifier signals; die level and hydraulic reservoir fluid level. Predetermined weld quality control limits are also stored on the data acquisition unit. The weld quality control limits are employed in evaluating the weld inspection data received from each weld scan.

During operation of the welding apparatus, an alarm indication is displayed to the welding apparatus operator if a signal which is outside of stored weld quality control limits is received from the EMAT receiver coil. Additionally, when such conditions exist, any one or more of the welding apparatus and/or welding process parameters corresponding to the welding apparatus and welding process data transmitted to the data acquisition unit may be automatically adjusted through computer control. Non-destructive test data indicating a defective weld, may in turn result in an automatic re-weld operation. The data acquisition unit is also used to collect and archive empirical data that may be used for later off-production line post-analysis, historical tracking and process monitoring.

A flat, plate-like, metal calibration station is also provided for practising the present invention. The calibration station may be employed either on or off the sheet metal processing line to check and adjust the EMAT transmitter and receiver coils and other weld inspection system electronics. On-line use of the calibration station may be made without adversely impacting production operations.

The various features of novelty which characterize the present invention are pointed out with particularity in the claims annexed to and forming a part of this disclosure. For a better understanding of the present invention, its advantages and specific objects attained by its uses, reference is made to the accompanying drawings and descriptive matter in which the preferred embodiment of the invention is illustrated.

DESCRIPTION OF THE PREFERRED EMBODIMENT

The present invention permits automated inspection of butt welds typically employed to join the ends of two sheet metal coils. A typical sheet metal production and treatment line on which the present invention may be utilized is comprised of a rolling mill, a plurality of roughing stands, a plurality of finishing stands, a first shearing apparatus, a welding apparatus, a temper mill, a pickling apparatus, a water rinse apparatus, a drying apparatus, a second shearing apparatus, a side splitter apparatus and a tandem cold mill. Frequently, a long flat sheet of metal produced by the rolling mill will be wound into a coil after passing through the finishing stands. The coil will then be transported to the first shearing apparatus located at another section of the factory and the end of that coil will be joined at the welding apparatus to the trailing end of another earlier transported coil which, for the most part, has already passed through a number of processing and treatment stations downstream of the welding apparatus. The location where the non-destructive weld test is made lies between the welding apparatus and the temper mill.

Figure 1:
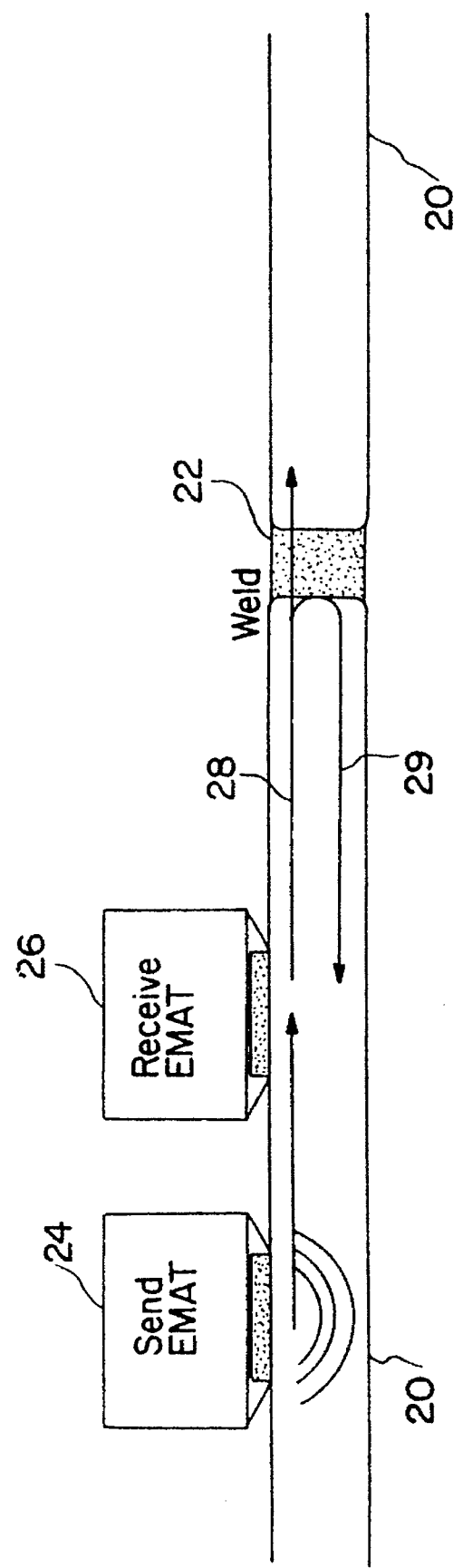
FIG. 1 is a schematic illustration displaying, in cross section, end portions of two sheet metal coils, joined by a butt weld and EMAT transmitter and receiver coils positioned near the weld, along with a one-dimensional path of travel of transmitted and reflected ultrasonic waves within the sheet metal.

FIG. 1 provides a cross sectional visualization of end portions (20) of two sheet metal coils, which are connected by a butt weld (22) made by the welding apparatus. Also shown in FIG. 1, are an EMAT transmitter coil (24) and an EMAT receiver coil (26), both of which are positioned just downstream of the butt weld (22) on a surface of the end portion (20) of one of the sheet metal coils. EMAT transmitter coil (24) produces an ultrasonic SH shear wave (28) which travels through end portion (20) toward butt weld (22) where a fraction of the SH shear wave (28) passes through the butt weld (22) and a fraction of the wave passes back through the end portion (20) and toward the EMAT receiver coil (26) as a reflected wave (29).

Figure 2:
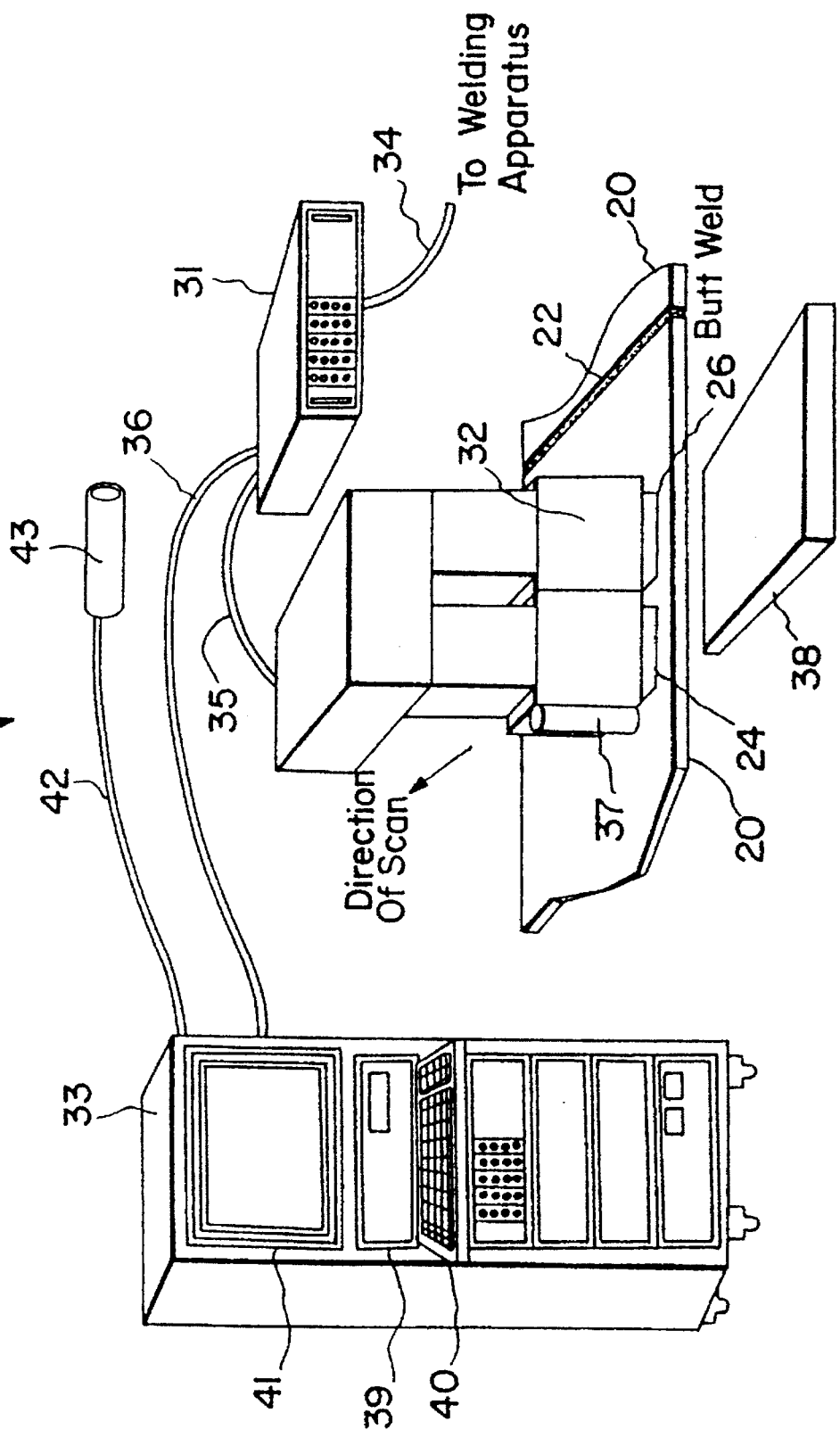
FIG. 2 is an illustration of the non-destructive weld inspection system employed with the present invention, pointing out the principal system components.

FIG. 2 illustrates the fundamental components of the weld inspection system used with the present invention. The weld inspection system has a computer control unit (31) which is in electrical communication with the welding apparatus, an L-shaped transport apparatus (32) and a data acquisition unit (33). A first cable (34) provides the electrical connection between the computer control unit (31) and the welding apparatus. A second cable (35) electrically connects the computer control unit (31) to the transport apparatus (32), and a third cable (36) links the computer control unit (31) to the data acquisition unit (33). The transport apparatus (32), which is positioned just down stream of the butt weld (22), has housed within one of its ends the EMAT transmitter coil (24) and the EMAT receiver coil (26). An edge detection sensor (37) is affixed to the transport apparatus in proximity of the EMAT transmitter coil (24). The edge detection sensor (37), which is in electrical communication with the computer control unit (31), is used to position the EMAT coils (24) and (26) at an edge of the end portion (20) of one of the sheet metal coils and to detect when the weld scan is complete.

Also shown in FIG. 2, is a flat, plate-like metal calibration station (38) which is used with the transport apparatus (32) to provide checkout and adjustment of the EMAT transmitter coil (24) and the EMAT receiver coil (26) as well as other system electronics. The data acquisition unit (33) includes a computer (39), a computer keyboard (40), a video display monitor (41) and a cable (42) having a connector (43), both of which provide for electrical connection of the data acquisition unit (33) to the welding apparatus.

While a specific embodiment of the invention has been shown and described in detail to illustrate the application of the principles of the invention, it will be understood that the invention may be embodied otherwise without departing from such principles.

What is claimed is:

1. An automated method for non-destructive inspection and evaluation of a butt weld used to join two coils of sheet metal end-to-end, the method comprising the steps of:

transmitting electronically from a welding apparatus to a data acquisition unit of a non-destructive weld inspection system information pertaining to the welding apparatus and to the process by which a butt weld has been made by the welding apparatus;

storing on the data acquisition unit the information transmitted from the welding apparatus to the data acquisition unit;

positioning near the butt weld a transport apparatus of the non-destructive weld inspection system, having a first and a second electromagnetic acoustic transducer (EMAT) attached to and housed within the transport apparatus;

scanning the butt weld with the transport apparatus while the first EMAT produces an ultrasonic SH shear wave which is transmitted through an end portion of a first sheet metal coil toward a weld joining the end portion of the first sheet metal coil to an end portion of a second sheet metal coil and while the second EMAT receives an ultrasonic SH shear wave which is reflected from the butt weld and which produces an electrical signal in the second EMAT;

transmitting to the data acquisition unit the electrical signal produced in the second EMAT;

recording on the data acquisition unit the electrical signal produced in the second EMAT;

analyzing in the data acquisition unit the electrical signal produced in the second EMAT;

signaling the presence of a defect in the weld when an analysis of the electrical signal produced in the second EMAT indicates a defect;

communicating electronically with the welding apparatus to reperform the butt weld and/or to alter the process for making one or more subsequent butt welds when the analysis of the electrical signal produced in the second EMAT indicates a defect.

2. A method according to claim 1, wherein a computer control unit of the non-destructive weld inspection system, which is in electrical communication with the welding apparatus, the transport unit and the data acquisition unit, initiates and implements positioning of the transport apparatus near the butt weld and thereafter commences scanning of the butt weld by the transport apparatus.

3. A method according to claim 2, wherein an electrical signal sent from the welding apparatus to the computer control unit upon completion of the butt weld is used to actuate positioning of the transport apparatus.

4. A method according to claim 3, wherein an edge detection sensor, which is attached to the transport unit and which is in electrical communication with the computer control unit, produces a first electrical signal used by the computer control unit to position the first EMAT and the second EMAT onto the surface of the end portion of the first sheet metal coil and near the butt weld before scanning commences.

5. A method according to claim 4, wherein the edge detection sensor produces a second electrical signal used by the computer control unit to disengage the first EMAT and the second EMAT from the surface of the end portion of the first sheet metal coil and to move the transport apparatus to a position away from the welding apparatus after scanning of the butt weld has been completed.

6. A method according to claim 5, wherein the first electrical signal is produced by the edge detection sensor when the edge detection sensor is moved near and detects a leading edge of the end portion of the first sheet metal coil and the second electrical signal is produced by the edge detection sensor when the edge detection sensor approaches and detects a trailing edge of the end portion of the first sheet metal coil.

7. A method according to claim 6, wherein the computer control unit is employed to receive the electrical signal produced by the second EMAT during scanning of the weld and to relay the signal to the data acquisition unit.

8. A method according to claim 7, wherein the data acquisition unit is comprised of a computer keyboard; a video display monitor; and a computer, such as a 486-based IBM/PC, having software capable of receiving, recording, monitoring and analyzing the electrical signal produced in the second EMAT and the information transmitted from the welding apparatus to the data acquisition unit.

9. A method according to claim 8, wherein the computer analyzes the electrical signal produced in the second EMAT relative to a plurality of weld quality control limits which have been preprogrammed into the computer.

10. A method according to claim 9, wherein the computer is employed to signal to an operator of the welding apparatus the presence and location of a defect in the butt weld when analysis of the electrical signal produced by the second EMAT discloses that a weld quality control limit has not been satisfied.

11. A method according to claim 10, wherein, when analysis of the electrical signal produced by the second EMAT discloses that a weld quality control limit has not been satisfied, the computer is also used to analyze the information transmitted to the data acquisition unit from the welding apparatus and to thereby determine whether and to what degree adjustments are needed to the welding apparatus and whether the butt weld should be remade.

12. A method according to claim 11, wherein the computer control unit is employed to communicate electronically with the welding apparatus and to convey specific adjustments which have been determined by the computer and instructions whether the butt weld should be remade.

13. A method according to claim 12, wherein a calibration station is employed to check and adjust either or both of the first EMAT coil and the second EMAT coil.

* * * * *